United States Patent [19]

Thornton

[11] Patent Number: 4,461,097

[45] Date of Patent: Jul. 24, 1984

[54] AERATOR

[75] Inventor: David C. Thornton, Erie, Pa.

[73] Assignee: American Sterilizer Company, Erie, Pa.

[21] Appl. No.: 336,053

[22] Filed: Dec. 31, 1981

[51] Int. Cl.$^3$ .......................... A61L 2/20; A61L 2/26; F26B 3/04; F26B 21/00

[52] U.S. Cl. .......................................... 34/233; 52/2; 312/31; 312/236; 422/34; 422/294; 422/295; 422/310

[58] Field of Search .................. 422/34, 294, 295, 310; 312/31, 31.04, 236; 52/2; 34/233

[56] References Cited

U.S. PATENT DOCUMENTS

| | | | |
|---|---|---|---|
| 3,114,599 | 12/1963 | Panning | 422/294 |
| 3,498,742 | 3/1970 | Long | 422/34 X |
| 3,554,688 | 1/1971 | Cassidy | 422/294 |
| 3,710,791 | 1/1973 | Denton | 52/2 X |

FOREIGN PATENT DOCUMENTS 236071 10/1960 Australia .............................. 422/294

Primary Examiner—Barry S. Richman
Attorney, Agent, or Firm—Robert D. Yeager; Andrew J. Cornelius

[57] ABSTRACT

An inflatable structure, includes a base and a barrier attached to the base which is capable of being inflated to a predetermined shape in order to define a chamber. A door in the barrier allows access to the chamber. The base includes a source of gas for inflating the barrier and for circulating within the chamber. The barrier is constructed as a twin-walled structure having inner and outer walls defining an air flow space therebetween. Holes are provided through at least portions of the inner wall to provide a means for circulation of air from the space into the chamber. When not in use, the aerator may be deflated and folded for compact storage and shipment.

6 Claims, 5 Drawing Figures

AERATOR

The Government has rights in this invention pursuant to Contract No. DAMD 17-79-C-9034 awarded by the United Sates Army.

BACKGROUND OF THE INVENTION

1. Field of the Invention

The invention relates generally to aerators and more specifically to aerators which can be collapsed for easy storage and shipment and inflated for use.

2. Description of the Prior Art

Items which have been sterilized by a gas such as ethylene oxide must be thoroughly aerated before use. Generally, the time required to aerate the sterilized articles is eight times the amount of time required to sterilize the articles. Therefore, so that the sterilizer capabilities may be utilized efficiently the volumetric capacity of the aeration equipment is normally many times that of the capacity of the associated gas sterilizer. In field use such as military hospitals the size and weight of the aeration equipment poses both transportation and storage problems. Accordingly, it is desired to have a portable, inflatable aerator which can be deflated for compact storage and shipment and inflated for use.

SUMMARY OF THE INVENTION

The present invention provides an inflatable structure which can be deflated from compact storage and shipment and inflated for use. The structure includes a base, a barrier attached to the base which is capable of being inflated to a predetermined shape in order to define a chamber, apparatus for permitting the chamber to be loaded and unloaded, apparatus for inflating and deflating the barrier and apparatus for circulating a gas within the chamber.

In one embodiment of the present invention the aerator includes a base and a double layered inflatable wall attached to the base. The base includes conventional apparatus to clean, heat and circulate the air and a power source.

Air supplied from the base into the space between the two layers of the wall thus causing the wall to inflate to form a chamber. Preferably, the wall is divided into a plurality of sections separated by seams. The sections are alternately either adapted to support the wall or provide circulating air to the chamber. The support sections are inflated with pressurized air. The inner layer in the circulating portions contain openings through which air can flow from the space between the two layers of the wall into the formed chamber to aerate the goods therein. The holes in the inner layer are sized and spaced so that the flow of air into the space between the two layers is greater than that from the space between the two layers into the chamber so as to create a back pressure within the space between the two layers thus keeping the wall inflated. Air also enters the chamber from openings in the base of the chamber. The spent air exits the chamber through an exhaust opening in the chamber and is vented to an area remote from the location of the aerator.

Alternatively, the inner layer in all portions of the wall can contain properly sized and spaced holes through which air can enter the chamber. In that case, only one source of circulating air is necessary.

DETAILED DESCRIPTION OF THE PREFERRED EMBODIMENTS

Figure 2:
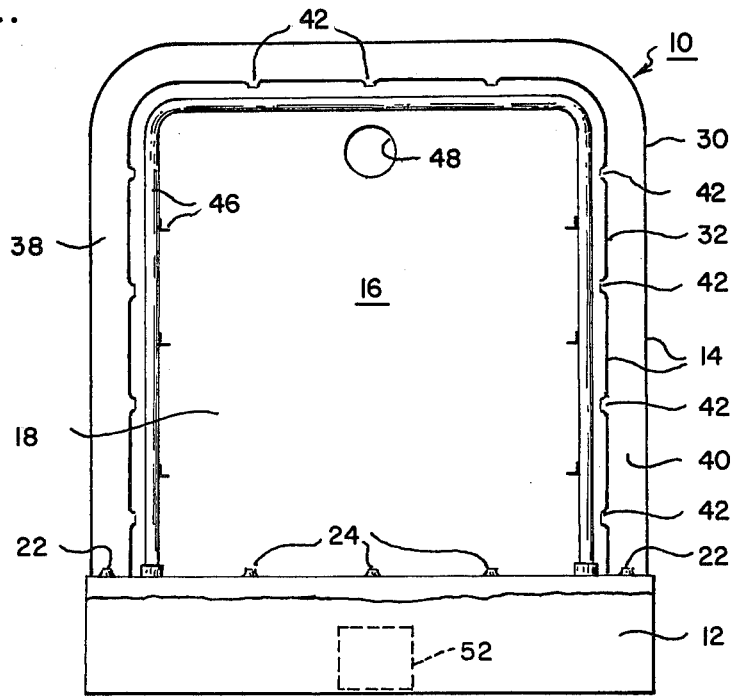
FIG. 2 is a transverse sectional view of the aerator through line II—II of FIG. 1.
Figure 1:
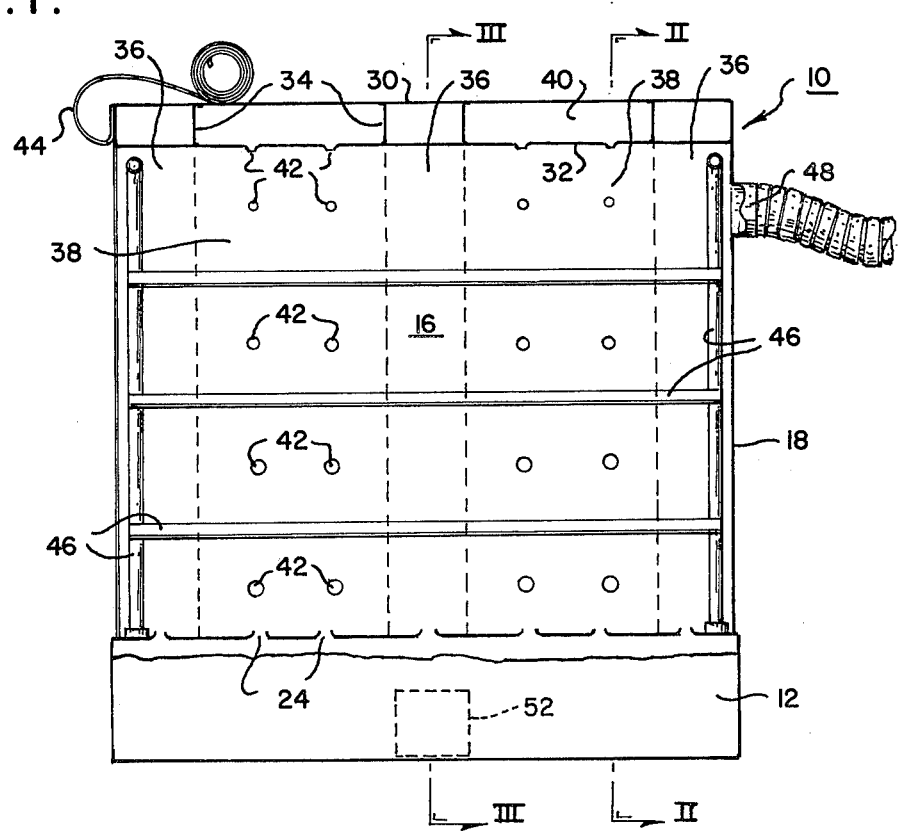
FIG. 1 is a longitudinal sectional view of the aerator according to the present invention.
Figure 3:
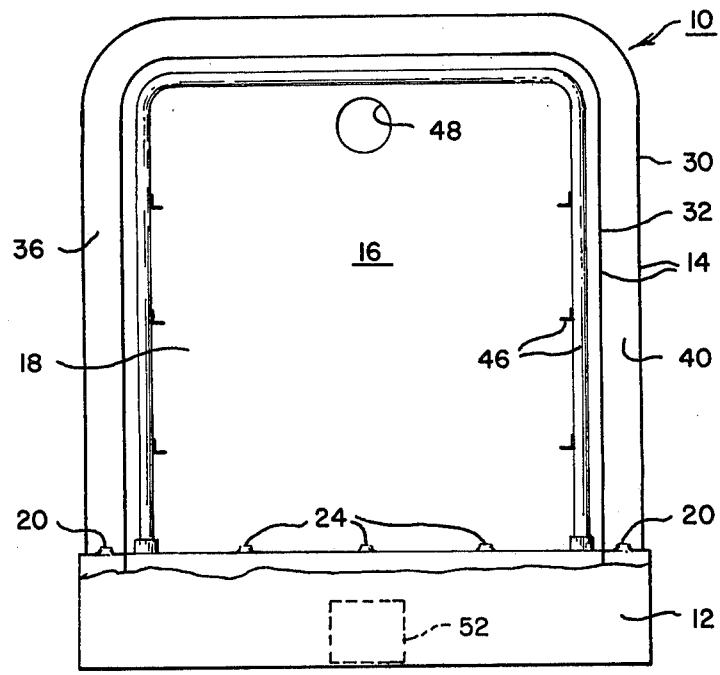
FIG. 3 is a transverse sectional view of the aerator through line III—III of FIG. 1.
Figure 5:
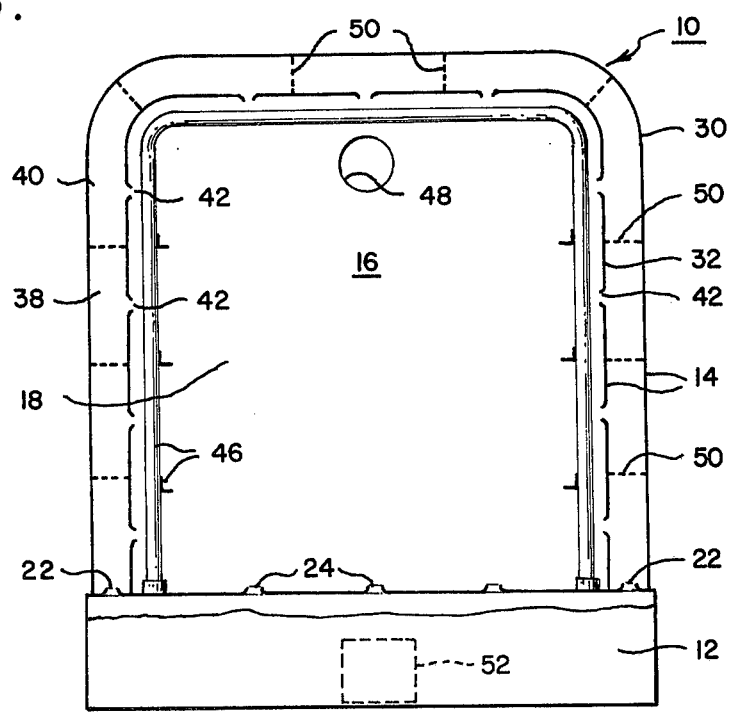
FIG. 5 is a transverse sectional view of the modified aerator through line V—V of FIG. 4.
Figure 4:
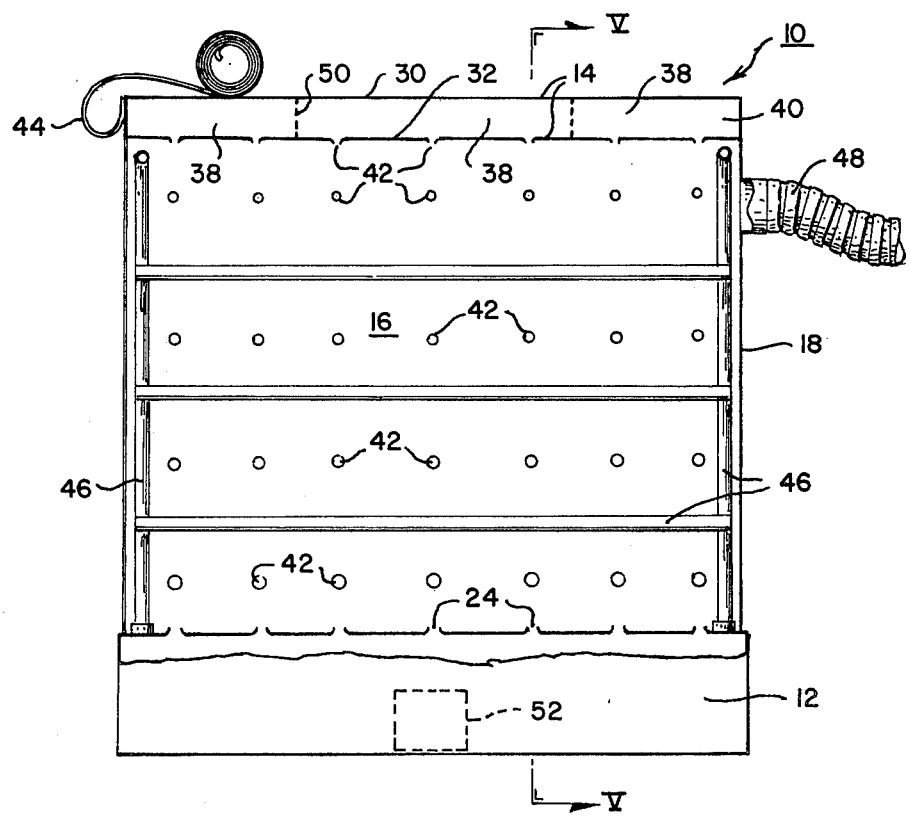
FIG. 4 is a longitudinal sectional view of a modified version of the aerator.

Referring to the drawings, aerator 10 includes cabinet module 12 and twin layered inflatable wall 14. When wall 14 is in its inflated condition, chamber 16 is formed. The top portion of cabinet module 12 forms the base of chamber 10.

Cabinet module 12 is preferably metal and contains a means of supplying pressurized air through openings 20 to inflate wall 14. In addition, cabinet module 12 includes a conventional heater, filter and blower 52 which cause clean, temperature controlled, heated air to be circulated through openings 22 to inflate wall 14 and aerate the goods loaded within chamber 16, and openings 24 through which the circulated air can enter chamber 16 directly from cabinet module 12 to aerate the goods loaded within chamber 16.

The two sides and top wall 14 include outer layer 30 and inner layer 32 made of a flexible, impervious plastic material. The two layers are held together by a plurality of seams 34 to prevent the layers from ballooning apart when wall 14 is inflated. Preferably, wall 14 is divided into five portions. Portions 36 receive pressurized air through openings 20 in cabinet module 12 and when inflated serve to support wall 14. Portions 38 receive clean, temperature controlled, heated air through openings 22 in cabinet module 12 and when inflated serve to support wall 14 and provide air to chamber 16. Preferably, the back panel 18 of wall 14 is a single layer of a flexible, impervious plastic material. When wall 14 is inflated, space 40 is formed between outer layer 30 and inner layer 32. Inner layers 32 of portions 38 contain a plurality of means for communicating air flow, such as openings 42 so that the circulating air can flow from space 40 through openings 42 into chamber 16. Wall 14 includes an opening through which chamber 16 can be loaded. Door 44, preferably formed of an insulated plastic material, is a flap attached to wall 14 above the opening in wall 14. When aerator 10 is in use door 44 extends down to cover and seal the opening in wall 14. Door 44 can be secured to wall 14 by hooks and fastener strips. Door 44 can be flipped over the top of aerator 10 to allow access to chamber 16.

Collapsible shelf support 46 can be placed within chamber 16 so that the goods to be aerated can be placed thereon. Duct hose 48 extends from an exhaust opening in panel 18 of wall 14.

In use, the blower, heater and filter contained within cabinet module 12 are operated by any conventional power source to provide pressurized air to wall portions 36 and to cause clean, heated, temperature controlled air to circulate through wall portions 38 and chamber 16. Pressurized air enters space 40 of wall portions 36 through openings 20 of cabinet module 12 thus causing wall portions 36 to inflate. The circulating air enters space 40 of wall portions 38 through openings 22 of cabinet module 12 thus causing wall portions 38 to inflate. The air flows from space 40 through holes 42 in inner layer 32 of wall portions 38 into chamber 16. The volume of air flowing from space 40 through openings 42 into chamber 16 is less than that flowing from cabinet module 12 into space 40 through openings 20 to create back pressure in space 40 in order to keep wall 14 inflated. The volume of air entering the lower portion of chamber 16 must be greater than that entering the top portion for the air to circulate properly, therefore, openings 42 are larger or more numerous in the lower portion of wall portions 38 than the upper portion of wall portions 38. Circulating air also flows directly into chamber 16 from cabinet module 12 through openings 24. The spent air exits chamber 16 through an exhaust opening in panel 18 and duct hose 48 and is vented to an area remote from the location of the aerator.

When aerator 10 is not in use, wall 14 can be deflated and folded for compact storage and shipment.

In a modified embodiment of the invention, as shown in FIGS. 4 and 5, inflatable wall 14 is separated into a plurality of sections 38 each of which receives clean, temperature controlled heated air through openings 22 in base 12. Inner layers 32 of sections 38 contain a plurality of openings 42 so that the circulating air can flow from space 40 through openings 42 into chamber 16. The air flow through sections 38 serves to inflate sections 38 and to provide circulating air to chamber 16 as described in the preferred embodiment. In addition, seams 34 are replaced by a plurality webs 50. Webs 50 serve to prevent layers 30 and 32 from ballooning apart as wall 14 is inflated.

What is claimed is:

1. An inflatable aerator comprising:

a base;

an inflatable twin walled barrier attached to said base such that a chamber is defined within said barrier when said barrier is inflated to a predetermined shape, said barrier being formed of an inner layer and an outer layer such that a space is defined therebetween;

means for permitting loading and unloading of said chamber;

means for causing air to flow from said base into said space between said inner layer and said outer layer of said barrier at sufficient pressure to inflate said barrier and for causing air to flow from said base through said chamber;

said inner layer of said barrier having a plurality of means for communicating air flow from said space through said chamber, said communicating means being arranged such that the number and size of said communicating means decreases as the portion of said inner layer having such communicating means extends further away from said base, thereby providing a gradually decreasing rate of air flow from said space into said chamber as the distance from said base to said communicating means increases, such that optimum air circulation for aeration of the goods disposed within said chmaber is achieved; and means for allowing air to exit said chamber.

2. An aerator as recited in claim 1 wherein said means for causing air to flow from said base into said chamber and into said space, respectively, is a blower contained within said base.

3. An aerator as recited in claim 1 wherein collapsible shelf supports are mounted within said chamber.

4. An aerator as recited in claim 1 wherein said barrier has an opening through which said chamber can be loaded and unloaded, said opening being able to be sealed by a flap attached to said barrier adjacent said opening, said flap extending over said opening and including means to secure said flap over said opening and seal said opening when the aerator is in use.

5. An aerator as recited in claim 1 wherein said space between said inner layer and said outer layer of said barrier is divided into a plurality of first and second separate sections, said first sections being adapted to support said barrier in a predetermined shape when said barrier is inflated by retaining pressurized air therein, and said second sections being adapted to circulate air into said chamber, and where the holes in said inner layer are disposed in said second sections and are not disposed in said first sections.

6. An aerator as recited in claim 5 wherein the pressure of the air flow into said first sections is greater than the pressure of the air flow into said second sections.

* * * * *

UNITED STATES PATENT AND TRADEMARK OFFICE
CERTIFICATE OF CORRECTION

PATENT NO. : 4,461,097
DATED      : July 24, 1984
INVENTOR(S): David C. Thornton It is certified that error appears in the above—identified patent and that said Letters Patent is hereby corrected as shown below:

Col. 2, line 31, after "top" insert --of--;

Signed and Sealed this

Thirtieth Day of July 1985

[SEAL]

Attest:

DONALD J. QUIGG

Attesting Officer     Acting Commissioner of Patents and Trademarks